United States Patent
Meinzer et al.

(10) Patent No.: US 6,475,519 B1
(45) Date of Patent: *Nov. 5, 2002

(54) OIL-FREE PHARMACEUTICAL COMPOSITIONS CONTAINING CYCLOSPORIN A

(75) Inventors: Armin Meinzer, Buggingen (DE); Barbara Haeberlin, Riehen (CH)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,391

(22) PCT Filed: Jan. 28, 1998

(86) PCT No.: PCT/EP98/00453
§ 371 (c)(1),
(2), (4) Date: Apr. 13, 1999

(87) PCT Pub. No.: WO98/33512
PCT Pub. Date: Aug. 6, 1998

(30) Foreign Application Priority Data

Jan. 30, 1997 (GB) ............................................. 9701881
Feb. 7, 1997 (GB) ............................................. 9702594

(51) Int. Cl.$^7$ ............................ A61K 9/48; A61K 9/66; A61K 38/13
(52) U.S. Cl. ........................ 424/456; 424/451; 424/452; 424/455; 514/785; 514/962
(58) Field of Search ................................ 424/451, 452, 424/455, 456, 453, 454, 457

(56) References Cited

U.S. PATENT DOCUMENTS

| | | | |
|---|---|---|---|
| 3,288,824 A | 11/1966 | Mahler et al. ............ 260/410.6 |
| 3,813,345 A | 5/1974 | Urton ........................ 252/312 |
| 3,954,967 A | 5/1976 | Urton .......................... 424/81 |
| 4,073,943 A | 2/1978 | Wretlind et al. ............. 424/358 |
| 4,108,985 A | 8/1978 | Ruegger et al. ............. 424/177 |
| 4,146,499 A | 3/1979 | Rosano ....................... 252/186 |
| 4,156,719 A | 5/1979 | Sezaki et al. ................ 424/118 |
| 4,210,581 A | 7/1980 | Ruegger et al. .......... 260/112.5 |
| 4,220,641 A | 9/1980 | Traber et al. ................ 424/177 |
| 4,388,307 A | 6/1983 | Cavanak ..................... 424/177 |
| 4,390,548 A | 6/1983 | Yamato et al. .............. 424/321 |
| 4,482,576 A | 11/1984 | Boot et al. .................. 426/603 |
| 4,567,161 A | 1/1986 | Posanski et al. .............. 514/23 |
| 4,571,926 A | 2/1986 | Scully ......................... 53/525 |
| 4,652,406 A | 3/1987 | Lepper et al. ............ 260/410.9 |
| 4,695,450 A | 9/1987 | Bauer et al. ................... 424/22 |
| 4,719,239 A | 1/1988 | Muller et al. ................ 514/785 |
| 5,741,512 A | 4/1988 | Hauer et al. ................. 424/450 |
| 4,794,000 A | 12/1988 | Ecanow ....................... 424/457 |
| 4,797,272 A | 1/1989 | Linn et al. ..................... 424/59 |
| 4,797,273 A | 1/1989 | Linn et al. ..................... 424/59 |
| 4,798,823 A | 1/1989 | Witzel ......................... 514/11 |
| 4,803,081 A | 2/1989 | Falk et al. .................... 424/488 |
| 4,835,002 A | 5/1989 | Wolf et al. ................... 426/590 |
| 4,888,239 A | 12/1989 | Brox ......................... 428/402.2 |
| 4,914,188 A | 4/1990 | Dumont et al. .............. 530/317 |
| 4,963,367 A | 10/1990 | Ecanow ....................... 424/485 |
| 4,990,337 A | 2/1991 | Kurihara et al. ............. 424/427 |
| 4,996,193 A | 2/1991 | Hewitt et al. .................. 514/11 |
| 5,037,653 A | 8/1991 | Dawson ....................... 424/405 |
| 5,047,396 A | 9/1991 | Orban et al. .................. 514/11 |
| 5,051,402 A | 9/1991 | Kurihara et al. ............... 514/11 |
| 5,154,754 A | 10/1992 | Damo et al. ..................... 71/79 |
| 5,206,219 A | 4/1993 | Desai ............................ 514/3 |
| 5,338,761 A | 8/1994 | Nakajima et al. ............ 514/772 |
| 5,342,625 A | 8/1994 | Hauer et al. ................. 424/455 |
| 5,441,738 A | 8/1995 | Klein et al. ............... 424/195.1 |
| 5,525,590 A | 6/1996 | Bollinger et al. .............. 514/11 |
| 5,589,455 A | 12/1996 | Woo .............................. 514/11 |
| 5,614,491 A | 3/1997 | Walch et al. ................... 514/11 |
| 5,639,724 A | 6/1997 | Cavanak ....................... 514/11 |
| 5,652,212 A | 7/1997 | Cavanak et al. ............... 514/11 |
| 5,756,450 A | 5/1998 | Hahn et al. ..................... 514/9 |
| 5,759,997 A * | 6/1998 | Cavanak ....................... 514/11 |
| 5,766,629 A | 6/1998 | Cho et al. .................... 424/455 |
| 5,827,822 A | 10/1998 | Floc'h et al. .................. 514/11 |
| 5,834,017 A | 11/1998 | Cho et al. .................... 424/455 |
| 5,951,971 A | 9/1999 | Kawashima et al. ....... 424/78.04 |
| 5,962,019 A | 10/1999 | Cho et al. .................... 424/455 |
| 5,977,066 A | 11/1999 | Cavanak ....................... 514/11 |
| 5,985,321 A | 11/1999 | Brox et al. ................... 424/451 |
| 6,007,840 A | 12/1999 | Hauer et al. ................. 424/450 |
| 6,008,191 A | 12/1999 | Singh et al. .................... 514/9 |
| 6,008,192 A | 12/1999 | Al-Rizzak et al. ............. 514/11 |
| 6,258,808 B1 | 7/2001 | Hauer et al. ................. 514/227 |

FOREIGN PATENT DOCUMENTS

| | | |
|---|---|---|
| BE | 895724 | 7/1983 |
| CA | 1209361 | 8/1986 |
| CH | 240 789 | 5/1946 |
| CH | 641356 | 2/1984 |
| DE | 738604 | 8/1943 |
| DE | 3315805 | 11/1984 |
| DE | 4003844 | 8/1990 |
| DE | 4412201 | 11/1994 |
| DE | 19539860 | 5/1996 |
| EP | 274 431 | 7/1983 |

(List continued on next page.)

OTHER PUBLICATIONS

Anonymous, Research Disclosure No. 21143 Galenic Compositions Comprising Cyclosporin A [CS–A] (1981).

(List continued on next page.)

Primary Examiner—James M. Spear
(74) Attorney, Agent, or Firm—John D. Thallemer

(57) ABSTRACT

The present invention provides a hard gelatine capsule containing a pharmaceutical composition comprising cyclosporin A in a mixture with a surfactant of HLB value of at least 10, substantially free of any oil and when a hydrophilic phase is present, the hydrophilic phase being a polyethylene glycol and/or a lower alkanol provided that any lower alkanol, if present, is present in less than 12% of the total weight of the composition absent the hard gelatine capsule.

11 Claims, No Drawings

FOREIGN PATENT DOCUMENTS

| | | |
|---|---|---|
| EP | 135 171 | 3/1985 |
| EP | 170 623 | 2/1986 |
| EP | 211 258 | 2/1987 |
| EP | 256 856 | 2/1988 |
| EP | 314 689 B1 | 5/1989 |
| EP | 315 079 | 5/1989 |
| EP | 327 280 | 8/1989 |
| EP | 361 928 | 4/1990 |
| EP | 378 893 | 7/1990 |
| EP | 589 843 | 3/1994 |
| FR | 2553661 | 4/1985 |
| GB | 616190 | 1/1949 |
| GB | 1171125 | 11/1969 |
| GB | 1516348 | 7/1978 |
| GB | 2015339 | 9/1979 |
| GB | 2098865 | 12/1982 |
| GB | 2120935 | 12/1983 |
| GB | 2206119 | 12/1988 |
| GB | 2209671 | 5/1989 |
| GB | 2211408 | 7/1989 |
| GB | 2211848 | 7/1989 |
| GB | 2218334 | 11/1989 |
| GB | 2221157 | 1/1990 |
| GB | 2222770 | 3/1990 |
| GB | 2224205 | 5/1990 |
| GB | 2228198 | 8/1990 |
| GB | 2230440 | 10/1990 |
| JP | 61/249918 | 11/1986 |
| JP | 61/280435 | 12/1986 |
| WO | 86/02264 | 4/1986 |
| WO | 87/01035 | 2/1987 |
| WO | 88/00059 | 1/1988 |
| WO | 90/08537 | 8/1990 |
| WO | 91/08676 | 6/1991 |
| WO | 92/09299 | 6/1992 |
| WO | 93/20833 | 10/1993 |
| WO | 95/11039 | 4/1995 |
| WO | 96/36316 | 11/1996 |
| WO | 97/00080 | 1/1997 |
| WO | 97/34622 | 9/1997 |
| WO | 98/40051 | 9/1998 |
| WO | 98/40094 | 9/1998 |

OTHER PUBLICATIONS

Beyer et al., "Mikroemulsionen" Pharmazie In Unserer Zeit, No. 2, pp. 55–60 (1983) –Translation.

Bhargava et al., "Using Microemulsions for Drug Delivery", Pharmaceutical Technology, pp. 46, 48, 50, 52, 54 (1987).

Cavanak et al., "Formulation of Dosage Forms" Prog. Allergy, vol. 38, pp. 65–72 (1986).

Ekman, [$^3$H]Cholesterol Transfer from Microemulsion Particles of Different Sizes to Human Fibroblasts, Lipids, vol. 22, No. 9, pp. 657–663 (1987).

Ritschel et al., Pharmaceutical Research, vol. 5, No. 10, Suppl. 108 PD 943 (1988).

Stupar et al., "Production of Micro–Emulsion Gels Using TEGO® Surfactants", Goldschmidt Inforwist Essein., vol. 52, pp. 22–28 (1982) –Translation.

Hahn, Biodegradable Tensides (1988).

Jayakrishnan et al., "Microemulsions: Evolving Technology for Cosmetic Applications", J. Soc. Cosmet. Chem., vol. 34, pp. 335–350 (1983).

Mubarak, Development and Testing of New Micro–Emulsions (1982).

Muller et al., Pharm. Ind., vol. 50, No. 11, pp. 1301–1306 (1988) –Translation.

Muller et al., Pharm. Ind., vol. 50, No. 3, pp. 370–375 (1988) Translation.

Pohler, Micro–Emulsion Gels Structural Investigations and Galenical Properties (1983).

Remington's Pharmaceutical Sciences, 17th Edition (A.R. Gennaro, Ed.), Microemulsions, Chapter 20, pp. 298–299, Easton, Pennsylvania (1985).

Reymond et al., "In Vitro Model for Ciclosporin Intestinal Absorption in Lipid Vehicles", Pharmaceutical Research, vol. 5, No. 10, pp. 673–676 (1988).

Reymond et al., "In Vivo Model for Ciclosporin Intestinal Absorption in Lipid Vehicles", Pharmaceutical Research, vol. 5, No. 10, pp. 677–679 (1988).

Reymond, In Vitron In Vivo Model for the Absorption of Cyclosporin A, Inaugural Dissertation, Basel, Switzerland (1986).

Ritschel et al., "Study on the Peroral Absorption of the Endekapeptide Cyclosporine A", Meth. Find. Exp. Clin. Pharmacol., vol. 11, No. 4, pp. 281–287 (1989).

Ritschel et al., "Improvement of Peroral Absorption of Cyclosporine A by Microemulsions", Meth. Find. Exp. clin. Pharmacol., vol. 12, pp. 127–134 (1990).

Ritschel, "Microemulsions for Improved Peptide Absorption from the Gastrointestinal Tract", Meth. Find. Exp. Clin. Pharmacol., vol. 13, No. 13, pp. 205–220 (1991).

Takada et al., Increased Systemic Availability of Cyclosporin A by Formulation Design: Pharmacokinetic Consideration on its Transport, Int. J. of Pharmaceutics, vol. 44, pp. 107–116 (1988).

Takada et al., "Enhanced Selective Lymphatic Delivery of Cyclosporin A by Solubilizers and Intensified Immunosuppressive Activity Against Mice Skin Allograft", Pharmaceutical Research, vol. 3, No. 1, pp. 48–51 (1986).

Takada et al., "Biological and Pharmaceutical Factors Affecting the Absorption and Lymphatic Delivery of Ciclosporin A from Gastrointestinal Tract", J. Pharmacobio-Dyn., vol. 11, pp. 80–87 (1988).

Takada et al., "Promotion of the Selective Lymphatic Delivery of Cyclosporin A by Lipid–Surfactant Mixed Micelles", J. Pharmacobio–Dyn., vol. 8, pp. 320–323 (1985).

Takada et al., "Effect of Administration Route on the Selective Lymphatic Delivery of Cyclosporin A by Lipid–Surfactant Mixed Micelles", J. Pharmacobio–Dyn., vol. 9, pp. 156–160 (1986).

Tarr et al., "Enhanced Intestinal Absorption of Cyclosporine in Rats Through the Reduction of Emulsion Droplet Size", Pharmaceutical Research, vol. 6, No. 1, pp. 40–43 (1989).

Yanagawa et al., "Selective Transfer of Cyclosporin to Thoracic Lymphatic Systems by the Application of Lipid Microspheres", J. Microencapsulation, vol. 6, No. 2, pp. 161–164 (1989).

Ziegenmeyer et al., Acta Pharmaceutica Technologica, vol. 26, No. 4, pp. 273–275 (1980) –Translation.

Ulman's Encyclopedia of Industrial Pharmacy, vol. A9, pp. 298–299 and 308–311 (1987).

Carrigan et al., "Biopharmaceutics of Drugs Administered in Lipid–Containing Dosage Forms I: GI Absorption of Griseofulvin from an Oil–In–Water Emulsion in the Rat", J. Pharm. Sci., vol. 62, pp. 1476–1479 (1973).

Frazer et al., "Emulsification of Fat in Intestine of the Rat and Its Relationship to Absorption", J. Physiol. vol. 103, pp. 306–316 (1944).

Drewe et al., "The Absorption Site of Cyclosporin in the Human Gastrointestinal Tract", Br. J. Clin. Pharmac., vol. 33, pp. 39–43 (1992).

Charley, Food Science, 2nd Edition, John Wiley & Sons, pp. 224, 226, 228–229 (1982).

The Merck Index, 9th Edition (M. Windhold, Ed.), Merck & Co., Inc., Rahway, NJ, p. 1017 (1976).

Takada, "Development of a New Carrier for Cyclosporine A With Selectivity for Lymphatics", Transp. Proceed., vol. XIX, No. 1, pp. 1711–1712 (1987).

Yasumura et al., "Take–Prolongation Effect for Transplanted Heart in Same–Species Rats by Lymph–Directive Cyclosporin Preparation", Igakunoayuni, vol. 136, pp. 455–456 (1986) –Translation.

* cited by examiner

OIL-FREE PHARMACEUTICAL COMPOSITIONS CONTAINING CYCLOSPORIN A

This application is a 371 of PCT/EP98/00453 filed Jan. 28, 1998.

The present invention relates to novel pharmaceutical compositions comprising cyclosporin A, also known as ciclosporine, as active agent (hereinafter referred to as cyclosporin).

Hitherto few pharmaceutical compositions containing cyclosporin have been accepted for commercial use for humans. Thus in the USA only SANDIMMUNE and NEORAL (cyclosporin for microemulsion) have been approved.

These formulations are available in the form of a drink solution or a soft gelatine capsule. Such soft gelatine capsules require special manufacturing techniques.

The compositions of the present invention are compositions containing cyclosporin which meet the requirements for approval in the US or elsewhere, yet can be produced in a form administrable as a hard gelatine capsule. Such capsules are well known in the art and may be made and filled in conventional manner.

In one aspect to present invention provides an oral pharmaceutical composition comprising cyclosporin A in a mixture with (i) a surfactant of HLB value at least 10, and optionally (ii) a viscosity increasing agent and/or (iii) a hydrophilic phase, the hydrophilic phase being a polyethylene glycol and/or a lower alkanol provided that any lower alkanol present is present in less than 12%, preferably less than 10 or 8% of the total weight of the composition, the composition being adapted for filling into, and serving as a centre-fill for, a hard gelatine capsule, and being substantially free of any additional oil.

The present compositions are based on the use of very few components, e.g. a surfactant (including associated side products normally arising from its preparation), optionally a viscosity increasing agent (thickener) and if desired an additional hydrophilic phase (additional to that present in the surfactant) chosen from polyethylene glycol and/or a lower alkanol which said lower alkanol is present in an amount of less than 12%, e.g. 8% by weight of the composition.

Cyclosporin compositions which have been proposed before suffer from the disadvantage that they are not stable in hard gelatine capsules, e.g. over 2 to 3 years and have bioavailability or variability similar to SANDIMMUNE OR NEORAL. The present compositions have excellent stability. The capsules do not become brittle.

Preferably the composition contains few other excipients. This has the advantage of reducing bulk. Thus preferably less than 5%, preferably less than 2% or 1% of lipophilic moieties (oils) apart from those present in the surfactant, or hydrophilic moieties, e.g. alkanols such as ethanol or propylene glycol are present.

The compositions may contain polyethylene glycol. This may be a part of the surfactant for example if this is produced by polyethoxylation or added separately. This may be present from e.g. 1 to 40% of the formulation. Preferably the polyethylene glycol is liquid at 37° C. e.g. having a M.W. 200 to 600 daltons.

The cyclosporin may be present in the usual dosage form for a cyclosporin formulation e.g. 25 mg; 50 mg; 100 mg per weight dosage form. The dosage form is e.g. a hard gelatine capsule as known in the art.

By the present invention there are provided novel cyclosporin galenic formulations, which meet or substantially reduce difficulties in cyclosporin, therapy hitherto encountered in the art. In particular it has been found that the compositions of the invention permit the preparation of solid, semi-solid and liquid compositions containing a cyclosporin in sufficiently high concentration to permit convenient oral administration, while at the same time achieving improved efficacy, e.g. in terms of bioavailability characteristics.

More particularly it has been found that compositions in accordance with the present invention enable effective cyclosporin dosaging with concomitant enhancement of resorption/bioavailability levels, as well as reduced variability in resorption/bioavailability levels achieved both for individual patients receiving cyclosporin therapy as well as between individuals. By application of the teachings of the present invention cyclosporin dosage forms are obtainable providing reduced variability in achieved cyclosporin blood/blood serum levels between dosages for individual patients as well as between individuals/ individual patient groups. The invention thus enables reduction of cyclosporin dosage levels required to achieve effective therapy. In addition it permits closer standardisation as well as optimisation of on-going daily dosage requirements for individual subjects receiving cyclosporin therapy as well as for groups of patients undergoing equivalent therapy.

By closer standardisation of individual patient dosaging rate and blood/blood-serum level response, as well as dosaging and response parameters for patient groups, monitoring requirements may be reduced, thus substantially reducing the cost of therapy.

By reduction of required cyclosporin dosaging/standardisation of achieved bio-availability characteristics, the present invention also offers a means permitting reduction in the occurrence of undesirable side-effects, in particular nephrotoxic reaction, in patients undergoing cyclosporin therapy.

The present compositions are of a small volume, yet stable, thereby increasing patient compliance.

The surfactant is preferably approved by the FDA, e.g. a GRAS surfactant, e.g.

1.1 Polyethyloxylated castor oil, e.g. reaction products of natural or hydrogenated vegetable oils and ethylene glycol, i.e. polyoxyethylene glycolated natural or hydrogenated vegetable oils, for example polyoxyethylene glycolated natural or hydrogenated castor oils. Such products may be obtained in known manner, e.g. by reaction of a natural or hydrogenated castor oil or fractions thereof with ethylene oxide, e.g. in a molar ratio of from about 1:35 to about 1:60, with optional removal of free polyethyleneglycol components from the product, e.g. in accordance with the methods disclosed in German Auslegeschriften 1,182,388 and 1,518,819. Especially suitable are the various tensides available under the trade name Cremophor. Particularly suitable are the products Cremophor RH 40 having a saponification no. ca. 50–60, an acid no.=<1, an iodine no.=<1, a water content (Fischer)=<2%, an $n_D^{60}$=ca. 1,453–1,457 and an HLB= ca. 14–16; Cremophor RH 60 having a saponification no.=ca. 40–50, an acid No.=<1, an iodine no.=<1, a water content (Fischer)=ca. 4.5–5.5%, an $n_D^{25}$=ca. 1,453–1,457 and an HLB=ca. 15–17; and Cremophor EL having a molecular weight (by steam osmometry)=ca. 1630, a saponification no.=ca. 65–70, an acid no.=ca. 2, an iodine no.=ca. 28–32 and an $n_D^{25}$=ca. 1.471 (c.f. Fiedler loc. cit. pp. 326–327). Also suitable for use in this category are the various tensides available under the trade name Nikkol, e.g. Nikkol HCO-60. The said product Nikkol HCO-60 is a reaction product of hydrogenated castor oil and ethylene oxide exhibiting the following characteristics: Acid no.=ca. 0.3; Saponification no.=ca. 47.4; Hydroxy value=ca. 42.5; pH (5%)=ca. 4.6; Color APHA=ca. 40; m.p.=ca. 36.0 C.; Freezing point=ca. 32.4 C.; $H_2O$ content (%, KF)=ca. 0.03;

Such products contain a "hydrophilic portion" of ca. 70 to 90% of fatty acid esters of glycerol polyethylene glycol, as well as fatty acid esters of polyethylene glycols and a hydrophilic portion of polyethylene glycol and glycerol ethoxylates. See for example Karl Müller, Tenside, Year 3, Issue 2, p. 37–45.

Preferably the surfactant is a polyethoxylated hydrogenated castor oil Cremophor RH.

1.2 Polyoxyethylene-sorbitan-fatty acid esters (polysorbates) e.g. produced by co-polymerising ethylene oxide with fatty acid esters of a sorbitol and its anhydrides of e.g. mono- and tri-lauryl, palmityl, stearyl and oleyl esters e.g. of the type known and commercially available under the trade name Tween (c.f. Fiedler, loc. cit. pp. 1300–1304) including the products Tween 20 [polyoxyethylene(20)sorbitanmonolaurate],
40 [polyoxyethylene(20)sorbitanmonopalmitate],
60 [polyoxyethylene(20)sorbitanmonostearate],
80 [polyoxyethylene(20)sorbitanmonooleate],
65 [polyoxyethylene(20)sorbitantristearate],
85 [polyoxyethylene(20)sorbitantrioleate],
21 [polyoxyethylene(4)sorbitanmonolaurate],
61 [polyoxyethylene(4)sorbitanmonostearate], and
81 [polyoxyethylene(5)sorbitanmonooleate].

Especially preferred products of this class for use in the compositions of the invention are the above products Tween 40 and Tween 80;

1.3 Polyoxyethylene fatty acid esters, e.g. produced by reacting fatty acids with ethylene oxide, e.g. polyoxyl 40 stearate, for example polyoxyethylene stearic acid esters of the type known and commercially available under the trade name Myrj (c.f. Fiedler, loc. cit., p. 834) as well as polyoxyethylene fatty acid esters known and commercially available under the trade name Cetiol HE. (c.f. Fiedler, loc. cit., p. 284); an especially preferred product of this class for use in the compositions of the invention is the product Myrj 52 having a $D^{25}$=ca. 1.1., m.p.=ca. 40–44C., an HLB=ca. 16.9., an acid no.=ca. 0–1 and a saponification no.=ca. 25–35;

1.4 Polyethoxylated glyceryl fatty acid mono esters, e.g. of lauryl, stearic, oleyl, or isostearic acid, e.g. those obtainable under the name Tagat O or L.

1.5 Polyoxyethylene mono esters of a saturated $C_{10}$ to $C_{22}$, e.g. $C_{18}$ substituted e.g. hydroxy fatty acid; e.g. 12 hydroxy stearic PEG acid, e.g. of PEG about e.g. 600–900 e.g. 660 daltons MW, e.g. SOLUTOL H515 from BASF, Ludwigshafen, Germany.

1.6 Polyoxyethylene-polyoxypropylene co-polymers, poloxamers, e.g. of the type known and commercially available under the trade names Pluronic and Emkalyx (c.f. Fiedler, loc. cit., pp. 956–958). An especially preferred product of this class for use in the compositions of the invention is the product Pluronic F68 (poloxamer 188).

1.7 Propylene glycol mono- and di-fatty acid esters such as propylene glycol dicaprylate, propylene glycol dilaurate, propylene glycol hydroxystearate, propylene glycol isostearate, propylene glycol laurate, propylene glycol ricinoleate, propylene glycol stearate and so forth (c.f. Fiedler, loc. cit, pp. 1013 et seq.). Especially preferred is propylene glycol caprylic-capric acid diester as known and commercially available under the trade name Miglyol 840 (c.f. Fiedler, loc. cit., p. 809). Miglyol 840 has a fatty acid content=$C_6$ max. ca. 3%, $C_8$ ca. 65–80%, $C_{10}$ ca. 15–30%, $C_{12}$ max. 3%. Acid no.=max. 0.1, iodine no.=ca. 320–340, iodine no.=max. 1.

Examples of ionic surfactants include:

2.1 Dioctylsuccinate, dioctylsodiumsulfosuccinate, di-[2-ethylhexyl]-succinate or sodium lauryl sulfate.

2.2 Phospholipids, in particular lecithins (c.f. Fiedler, loc. cit., pp. 731–733). Lecithins suitable for use in the compositions of the invention include, in particular, soya bean lecithins.

2.3 Bile salts, e.g. alkali metal salts, for example sodium taurocholate.

Examples of further lipophilic surfactants for use as surfactant component are, e.g.:

2.1 Trans-esterification products of natural vegetable oil triglycerides and polyalkylene polyols. Such transesterification products are known from the art and may be obtained e.g. in accordance with the general procedures described in U.S. Pat. No. 3,288,824. They include transesterification products of various natural (e.g. non-hydrogenated) vegetable oils for example, maize oil, kernel oil, almond oil, ground nut oil, olive oil and palm oil and mixtures thereof with polyethylene glycols, in particular polyethylene glycols having an average molecular weight of from 200 to 800. Preferred are products obtained by trans-esterification of 2 molar parts of a natural vegetable oil triglyceride with one molar part of polyethylene glycol (e.g. having an average molecular weight of from 200 to 800). Various forms of trans-esterification product of the class defined are known and commercially available under the trade name Labrafil [see Fiedler, loc. cit., 707]. Especially useful as components of the compositions of the invention are the products: Labrafil M 1944 CS, a trans-esterification product of kernel oil and polyethylene glycol having an acid no.=ca. 2, a saponification no. ca. 145–175 and an iodine no.=ca. 60–90; and Labrafil M 2130 CS, a trans-esterification product of a $C_{12}$- to $C_{18}$-glyceride and polyethylene glycol having a melting point=ca. 35–40 C., an acid no.=<2, a saponification no.=ca. 185–200 and an iodine no.=<3;

2.2 Mono-, di- and mono/di-glycerides, especially esterification products of caprylic or capric acid with glycerol. Preferred products of this class are e.g. those comprising or consisting mainly or essentially of caprylic/capric acid mono- and di-glycerides such as are commercially available under the trade name Imwitor (c.f. loc. cit., pp. 645). A particularly suitable product of this class for use in the compositions of the invention is the product Imwitor 742, which is the esterification product of a mixture of ca. 60 p.p.w. caprylic acid and ca. 40 p.p.w. capric acid with glycerol. Imwitor 742 is typically a yellowish crystalline mass, liquid at ca. 26 C.; acid no.=max. 2; iodine no.= max. 1; saponification no.=ca. 235–275: % monoglycerides=ca. 40–50%; free glycerol=max. 2%; m.p.=ca. 24–26C.; unsaponifiables=0.3% max.; peroxide no.=max. 1;

2.3 Sorbitan fatty acid esters e.g. of the type known and commercially available under the trade name Span, for example including sorbitan-monolauryl, -monopalmityl, -monostearyl, -tristearyl, -monooleyl and -trioleyl esters—(c.f. Fiedler, loc. cit., pp. 1139–1140);

2.4 Pentaerythritol fatty acid esters and polyalkylene glycol ethers, for example pentaerythrite-dioleate, -distearate, -monolaurate, -polyglycol ether and -monostearate as well as pentaerythrite-fatty acid esters (c.f Fiedler, loc. cit. pp. 923–924);

2.5 Monoglycerides, e.g. glycerol monooleate, glycerol monopalmitate and glycerol monostearate, for example as known and commercially available under the trade names Myvatex, Myvaplex and Myverol (c.f. Fiedler, loc. cit., pp. 836), and acetylated, e.g. mono-and di-acetylated monoglycerides, for example as known and commercially available under the trade name Myvacet (c.f. Fiedler, loc. cit., pp. 835);

2.6 Glycerol triacetate or (1,2,3)-triacetin (c.f. Fiedler, loc. cit., pp. 952); and 2.7 Sterols and derivatives thereof, for example cholesterols and derivatives thereof, in particular phytosterols, e.g. products comprising sitosterol, campesterol or stigmasterol, and ethylene oxide adducts thereof, for example soya sterols and derivatives thereof, such as known under the trade name Generol (c.f. Fiedler loc. cit., p.p. 554 and 555) in particular the products Generol 122, 122 E5, 122 E10, and 122 E25.

It is to be appreciated that surfactants may be complex mixtures containing side products or unreacted starting products involved in the preparation thereof made by e.g. polyoxyethylation may contain another side product, e.g. polyethylene glycol.

The compositions of the invention may also comprise a thickening agent (also referred to as a viscosity increasing agent).

Suitable thickening agents may be of those known and employed in the art, including e.g. pharmaceutically acceptable polymeric materials and inorganic thickening agents which enable the compositions to be filled easily and resists leakage, e.g. thixotropic agents. These should also have the property of dissolving quickly (e.g. within 5 minutes) in the stomach juices or water or at pH 1 to 2, for example, of the following types:

3.1 Water soluble tocopheryl polyethylene glycol succinic acid esters (TPGS), e.g. with a polymerisation number ca 1000, e.g. available from Eastman Fine Chemicals Kingsport, Tex., USA.

3.2 Water soluble celluloses and cellulose derivatives including; alkyl celluloses, e.g. methyl-, ethyl- and propyl-celluloses; hydroxyalkyl-celluloses, e.g. hydroxypropyl-celluloses and hydroxypropylalkyl-celluloses such as hydroxypropyl-methyl-celluloses; acylated celluloses, e.g. cellulose-acetates, cellulose-acetatephthallates, cellulose-acetatesuccinates and hydroxypropylmethyl-cellulose phthallates; and salts thereof such as sodium-carboxymethyl-celluloses. Examples of such products suitable for use in accordance with the present invention are those known and commercially available, e.g. under the trade names Klucel and Methocel (c.f. Fiedler, loc. cit., pp. 688 and 790), 3.3 Water soluble polyvinylpyrrolidones, including for example poly-N-vinylpyrrolidones and vinylpyrrolidone co-polymers such as vinylpyrrolidone-vinylacetate co-polymers, especially of low molecular weight. Examples of such compounds suitable for use in accordance with the present invention are those known and commercially available, e.g. under the trade name Kollidon (or, in the USA, Povidone) (c.f. Fiedler, loc. cit., pp. 694–696), in particular the products Kollidon 30 and 90;

3.4 Low amounts of inorganic thickening agents such as atapulgite, bentonite and silicates including hydrophilic silicon dioxide products, e.g. alkylated (for example methylated) silica gels, in particular colloidal silicon dioxide products as known and commercially available under the trade name Aerosil [c.f. Handbook of Pharmaceutical Excipients, loc. cit., p.p. 253–256] in particular the products Aerosil 130, 200, 300, 380, O, OX 50, TT 600, MOX 80, MOX 170, LK 84 and the methylated Aerosil R 972.

The compositions may also include one or more further ingredients e.g. in an amount of from 0.1 to 5%, in particular anti-oxidants [e.g. ascorbyl palmitate, butyl hydroxy anisole (BHA), butyl hydroxy toluene (BHT) and tocopherols, e.g. -tocopherol (vitamin E)], flavouring agents and so forth. Use of an anti-oxidant, in particular a tocopherol, is particularly advantageous.

The relative proportion of ingredients in the compositions of the invention will, of course, vary considerably depending on the particular type of composition concerned. Determination of workable proportions in any particular instance will generally be within the capability of the man skilled on the art. All indicated proportions and relative weight ranges described below are accordingly to be understood as being indicative of preferred or individually inventive teachings only and not as not limiting the invention in its broadest aspect.

a) The cyclosporin will generally be present in an amount of from 5 to 30%, suitably from about 10 to about 25% by weight based on the total weight of the composition absent the hard gelatine capsule.

b) Any polyethylene glycol amount when present will generally be present in an amount of from about 15% to about 30%, by weight based on the total weight of the composition absent the hard gelatine capsule;

c) Any further excipient apart from the surfactant and as thickening agent is preferably present from an amount from 0.1% to 5%, by weight based on the total weight of the composition absent the hard gelatine capsule.

The compositions above may additionally include a thickening agent, though, as previously indicated, this will generally be less preferred. The amount of thickening agent present may vary e.g. depending on the required consistency of the end product, e.g. whether it is to be in a thickened flowable form, for example for filling into a capsule. The amount will of course also depend on the nature of the thickening agent chosen. In general the thickeners components (4), when present will be present in an amount of up to about 25% by weight based on the total weight of the composition, more suitably in an amount of up to about 15 or 20% by weight, e.g. in an amount of from 0.5 or 5 up to 15 or 20% by weight based on the total weight of the composition.

The compositions may also include further additives or ingredients, e.g. as hereinbefore described. In particular they may comprise antioxidants, e.g. in an amount of up to about 0.5 or 1% by weight based on the total weight of the composition, and sweetening or flavouring agents, e.g. in an amount of up to about 2.5 or 5% by weight based on the total weight of the composition.

Preferably no other excipients are present. Thus the volume may be kept low and the composition may be filled into a capsule size, 1, 2 or 3.

The compositions have been found to exhibit especially advantageous properties when administered orally, e.g. in terms of both the consistency and high level of bioavailability achieved as defined in standard tests in humans or e.g. beagle dogs. In particular, and in contrast with other galenic systems, e.g. as known from the art, it has been found that such compositions are compatible with tenside materials, e.g. bile salts, present in the gastro-intestinal tract. That is, they are fully dispersible in aqueous systems comprising such natural tensides and are thus capable of providing microemulsion systems in situ which are stable and do not exhibit precipitation or other disruption of fine particulate structure. Function of such systems on oral administration remains independent of and/or unimpaired by the relative presence or absence of bile salts at any particular time or for any given individual. Such compositions accordingly represent an especially preferred embodiment of the invention. The bioavailability characteristics may be observed in standard clinical trials or in dogs using standard radioimmunoassays for cyclosporins. Preferred capsules have a short Tmax. Preferably the compositions form, on dilution with water, micellar solutions, in which one may be able to detect droplets of, e.g. from 10 to 150 nm in diameter.

The compositions above will preferably be compounded in orally administerable hard gelatine capsule shells to be unit dosage forms. Where the compositions are in unit dosage form, each unit dosage will suitably contain between about 5 or 10 and about 200 mg cyclosporin, more suitably between about 15 or 25 and about 15 mg, e.g. 25, 50 or 100 mg cyclosporin. Thus unit dosage forms in accordance with the invention, suitable for administration 1×, 2× or 3× up to 5× daily (e.g. depending on the particular purpose of therapy, the phase of therapy etc. . .) will appropriately comprise e.g. about 25 mg, about 50 mg or about 100 mg cyclosporin per unit dosage.

Further details of the excipients are given in Fiedler.

The following non-limitative Examples illustrate the invention.

EXAMPLE 1

| Hard gelatine capsules | |
| --- | --- |
| Cyclosporin A | 100 mg |
| Surfactant (Cremophor RH or Tween) | 300 mg |

EXAMPLE 2

As for Example 1 but containing additionally 10 mg of TPGS.

Each composition shows a bioavailability profile in humans and dogs similar to that of NEORAL, e.g. in terms of AUC, Tmax and Cmax.

The hard gelatine capsules are stable for at least 2 years and maintain an excellent condition.

EXAMPLE 3

| Hard gelatine capsules | |
| --- | --- |
| Cyclosporin A | 50 mg |
| Surfactant (Cremophor RH or Tween) | 300 mg |
| 1,2-Propylene glycol or Ethanol | 8% by weight of the total composition |

EXAMPLE 4

| Hard gelatine capsules | |
| --- | --- |
| Cyclosporin A | 50 mg |
| Surfactant (Cremophor RH or Tween) | 300 mg |
| PEG 300 | 30% by weight of the total composition |

We claim:

1. A hard gelatine capsule containing a pharmaceutical composition comprising:

a) cyclosporin A;

b) polyethyloxylated castor oil having an HLB value of at least 10; and c) a polyethylene glycol and a lower alkanol, wherein the polyethylene glycol is present in an amount of 1 to 40 weight percent, and each loweralkanol is present in an amount of less than 12 weight percent, wherein the weight percents are based on the total weight of the composition disregarding the hard gelatine capsule.

2. The hard gelatine capsule according to claim 1 wherein component (b) further comprises a polyoxyethylene-sorbitan fatty acid ester and a sorbitan fatty acid ester.

3. The hard gelatin capsule according to claim 2 wherein the polyoxyethylene-sorbitan fatty acid ester is polyoxyethylene(20)sorbitanmonooleate.

4. The hard gelatin capsule according to claim 2 wherein the sorbitan fatty acid ester is sorbitan-monooleyl ester.

5. The hard gelatine capsule according to claim 1 wherein the cyclosporin is present in an amount of from 10 to 25 weight percent, based on the total weight of the composition disregarding the hard gelatine capsule.

6. The hard gelatine capsule according to claim 1 wherein the polyethyloxylated castor oil is polyethoxylated hydrogenated castor oil.

7. The hard gelatine capsule according to claim 1 further comprising a thickening agent.

8. The hard gelatine capsule according to claim 7 wherein the thickening agent is a water soluble tocopheryl polyethylene glycol succinic acid ester.

9. The hard gelatine capsule according to claim 1 wherein the composition is a semi-solid with the cyclosporin dissolved therein.

10. The hard gelatine capsule according to claim 1 wherein the composition is a liquid with the cyclosporin dissolved therein.

11. The hard gelatine capsule according to claim 1 wherein the composition forms a microemulsion.

* * * * *